United States Patent [19]

Horlenko et al.

[11] 4,301,298

[45] Nov. 17, 1981

[54] LIGHT ENDS RECOVERY IN ETHYL ACRYLATE PROCESS

[75] Inventors: Theodore Horlenko, Corpus Christi; James L. Paul; James W. Gordon, both of Houston, all of Tex.

[73] Assignee: Celanese Corporation, New York, N.Y.

[21] Appl. No.: 152,885

[22] Filed: May 23, 1980

[51] Int. Cl.³ .................. C07C 67/48; B01D 3/10
[52] U.S. Cl. .................... 560/218; 560/205; 202/183; 202/205; 203/8; 203/39; 203/42; 203/80; 203/91; 417/68
[58] Field of Search .............. 202/205, 183; 203/91, 203/42, 39, 80, 8, 4, DIG. 22; 560/247, 248, 218, 205; 417/68, 69

[56] References Cited

U.S. PATENT DOCUMENTS

| | | | |
|---|---|---|---|
| 1,972,157 | 9/1934 | Miller | 203/91 |
| 2,336,493 | 12/1943 | Marks | 560/248 |
| 3,228,860 | 1/1966 | Larson | 202/205 |
| 3,248,233 | 4/1966 | Brent et al. | 417/68 |
| 3,951,756 | 4/1976 | Dirks et al. | 560/248 |
| 4,087,208 | 5/1978 | Uda et al. | 417/68 |

Primary Examiner—Wilbur L. Bascomb, Jr.
Attorney, Agent, or Firm—Stewart N. Rice; Ralph M. Pritchett

[57] ABSTRACT

A normally liquid hydrocarbon having a minimum boiling point of about 425° F. is utilized to provide the liquid seal in a vacuum pump which intakes a gaseous light ends stream resulting from a process for the production of ethyl acrylate by the reaction of ethylene with acrylic acid in the presence of a sulfuric acid catalyst. Upon contact in the vacuum pump, the gaseous light ends are partially absorbed into the normally liquid hydrocarbon, with the normally liquid hydrocarbon being recovered by fractionation.

13 Claims, 1 Drawing Figure

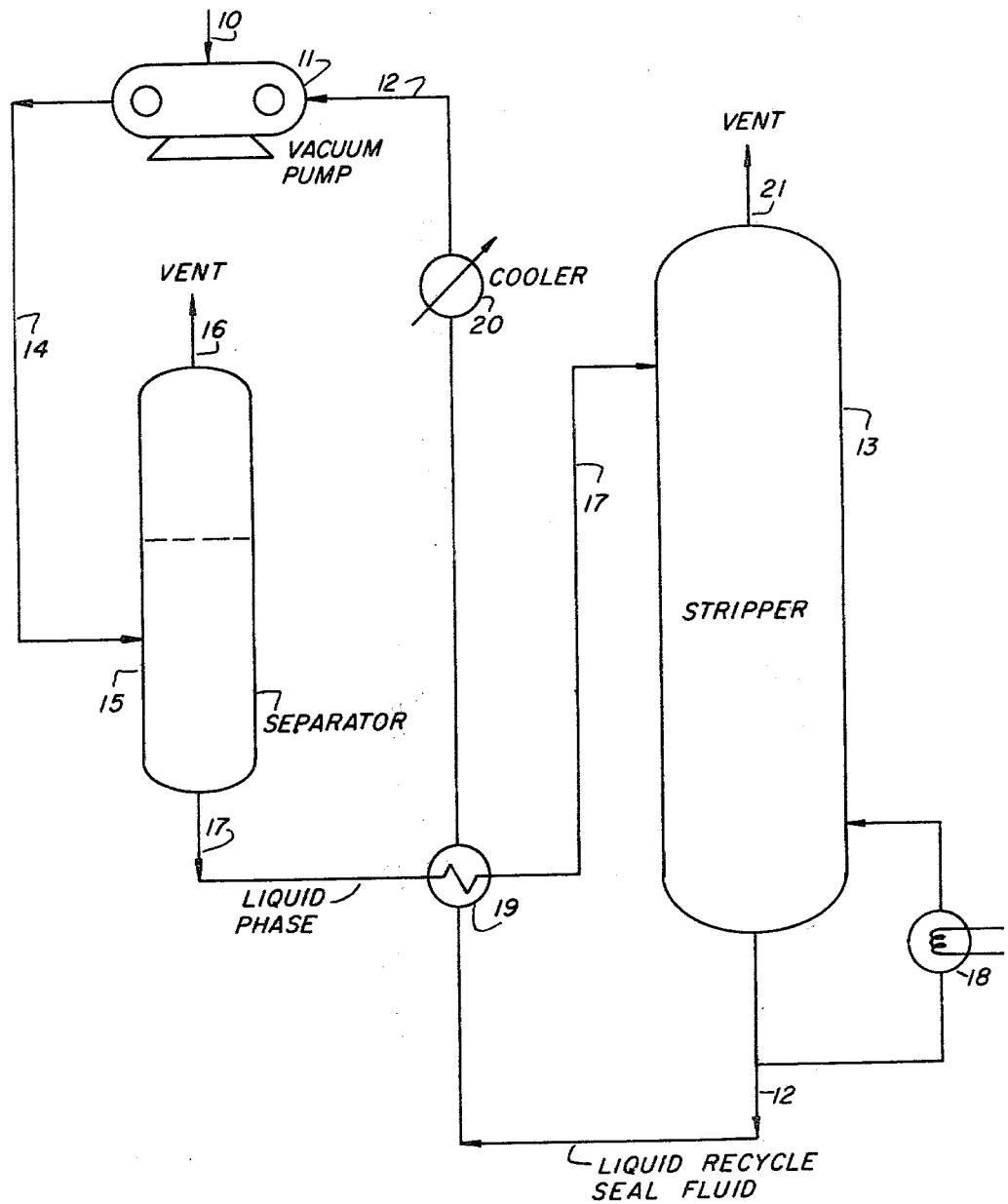

LIGHT ENDS RECOVERY IN ETHYL ACRYLATE PROCESS

BACKGROUND OF THE INVENTION

It is known in the prior art to produce ethyl acrylate by the reaction of ethylene with acrylic acid in the presence of a sulfuric acid catalyst. In this process recovery of a liquid ethyl acrylate product is accomplished by passing the reaction mixture to a vacuum distillation system wherein, at reduced pressures less than atmospheric, the reaction mixture is distilled to obtain a liquid ethyl acrylate product. Also resulting from the vacuum distillation is a gaseous light ends stream containing sulfur dioxide and also containing ethylene, ethyl acrylate and other organic light ends. The sulfur dioxide in the stream derives from the sulfuric acid catalyst used in the reaction of the ethylene and acrylic acid.

Since the distillation is accomplished under vacuum, which is necessarily provided by a vacuum pump (generally also known as a rotary compressor), the gaseous light ends removed as overhead products in the vacuum distillation system must necessarily be drawn into and passed through the vacuum pump. In the type of pump normally utilized for obtaining the vacuum there is generally employed a liquid seal fluid which provides a liquid seal (sometimes referred to as an "oil seal") within the pump whereby the vacuum may be obtained. Thus the vacuum pump must intake both a gaseous stream from the intake line or conduit which is in open communication with the vacuum distillation system, and also a liquid stream comprised of the liquid seal fluid. Within the vacuum pump the gaseous stream and the liquid seal fluid are intimately contacted with each other and then discharged in a single stream as a gas-liquid mixture. For efficient operation the liquid seal fluid must be recovered from the gas-liquid discharge and reused or recycled through the vacuum pump.

In many instances the recovery of the liquid seal fluid from the gas-liquid mixture is relatively easily accomplished by use of a simple separator; however in the above described process for production of ethyl acrylate many problems occur because of the nature of the gaseous light ends stream. More particularly, various components of the light ends stream are absorbed or partially absorbed into the liquid seal fluid and removal of these components cannot be accomplished merely through the use of a separator. In such instances, it is known to utilize distillation to separate absorbed components from the liquid seal fluid. Thus the choice of a liquid to be utilized to provide the liquid seal in the vacuum pump is quite important since various problems in the recovery and recycle of the liquid seal fluid can be eliminated or minimized by selection of the proper liquid. Many liquids have been found not to be suitable because of polymerization, foaming and other problems. It is believed that some of these problems can, at least in part, be attributed to the presence of the sulfur dioxide in the gaseous light ends.

It is thus an object of the present invention to provide and disclose the use of a liquid which performs satisfactorily as a liquid seal fluid for a vacuum pump utilized in the above described recovery of light ends from the ethyl acrylate process. It is an additional object of the present invention to provide an improved process for recovering the light ends stream from the said ethyl acrylate process and provide for recovery of the liquid seal fluid utilized in the vacuum pump providing the reduced pressure for the vacuum distillation system of the ethyl acrylate process. These and additional objects will become apparent from the following description of the present invention.

SUMMARY

The foregoing and additional objects are accomplished by the present invention which, in one of its aspects, is an improvement in a process for the production of ethyl acrylate by the reaction of ethylene with acrylic acid in the presence of a sulfuric acid catalyst wherein the reaction products are distilled in a vacuum distillation system at a reduced pressure less than atmospheric to obtain a liquid ethyl acrylate product and also resulting in a first gaseous light ends stream from said vacuum distillation system containing sulfur dioxide and containing ethylene, ethyl acrylate and other organic light ends by-products, which said first gaseous light ends stream passes through a vacuum pump providing the reduced pressure for said vacuum distillation system, which said vacuum pump utilizes a liquid seal fluid to provide a liquid seal therein and in which vacuum pump said first gaseous light ends stream mixes with and is partially absorbed in said liquid seal fluid to result in a gas-liquid mixture which is discharged from said vacuum pump, and which said gas-liquid mixture so discharged is fractionated to recover a liquid recycle stream comprising liquid seal fluid and which liquid recycle stream is recycled to said vacuum pump, which improvement comprises utilizing as said liquid seal fluid a normally liquid hydrocarbon which has a minimum boiling point of 425° F. and 90% by weight of which boils within the range of about 425° F. to 800° F.

DETAILED DESCRIPTION OF THE INVENTION

The present invention resides in the use of, and the discovery that the use of, a normally liquid hydrocarbon having certain characteristics will serve as and provide good performance as a liquid seal fluid in a vacuum pump used to provide the reduced pressure in the above described vacuum distillation system for recovery of light ends in the ethyl acrylate process. The normally liquid hydrocarbon must have certain characteristics and meet certain specifications in order to give satisfactory performance, and not all normally liquid hydrocarbons will be satisfactory. The term "normally liquid hydrocarbon" as used in the specification and in the claims is meant to include not only a liquid consisting of a single hydrocarbon compound, but also mixtures of various hydrocarbon compounds. In fact the usual normally liquid hydrocarbon commercially available for use in the invention, and most economical for use in the invention, is a petroleum distillate which will contain numerous hydrocarbon compounds having boiling points spread over a range of temperatures. For example, a typical "cut" derived from the distillation of petroleum and suitable for use in the invention may first begin to boil at 500° F., with the final portions boiling off at 550° F. By "normally liquid" as used in the specification and in the claims is meant liquid at 25° C. and atmospheric pressure.

The normally liquid hydrocarbon should be one which has a minimum boiling point of at least 425° F., preferably at least 460° F., and at least 90%, preferably substantially all, of the hydrocarbon should boil within the range of about 425° F. to 800° F., preferably within the range of about 460° F. to 750° F. All boiling points disclosed in the specification and referrred to in the claims are meant to refer to the boiling point at atmospheric pressure. If the hydrocarbon has a minimum boiling point of less than about 425° F., then problems are presented in the separation of the components derived from the ethyl acrylate light ends stream. A normally liquid hydrocarbon which has too high a boiling point can also present problems since many of these high boilers are too viscous for proper performance as a liquid seal in the vacuum pump.

The normally liquid hydrocarbon can be aromatic or nonaromatic, saturated or unsaturated, or contain mixtures of all the foregoing. As pointed out above, most "cuts" of petroleum distillate will contain numerous compounds and these may be of various types. The preferred hydrocarbon will be one which is substantially free of ethylenic unsaturation and of acetylenic unsaturation. Viscosity of the hydrocarbon is also of consideration since it can effect its function as the liquid seal in the vacuum pump.

Reference is now made to FIG. 1 for an explanation of a process conducted in accordance with the invention. A gaseous light ends stream 10 derived from the vacuum distillation system of the above described ethyl acrylate process is drawn into rotary compressor or vacuum pump 11 which provides the vacuum for the vacuum distillation system. This light ends stream would generally contain sulfur dioxide, ethylene, ethyl acrylate, ethyl acetate, diethyl ether and ethanol. Since there are usually various air leaks in the vacuum distillation system, nitrogen and oxygen will usually also be present in the light ends stream in atmospheric ratios.

Also fed or passed to vacuum pump 11 through line 12 is a liquid stream comprised of the liquid seal fluid which is recycled from the base of distillation tower 13. Within vacuum pump 11 the gaseous light ends from stream 10 and the liquid seal fluid from line 12 are intimately contacted and mixed with each other to form a gas-liquid mixture, and the gas-liquid mixture discharged from vacuum pump 11 through line 14. In the contact of the light ends with the seal fluid, a portion of the components of the light ends stream 10 are dissolved by and absorbed into the liquid.

The gas-liquid mixture discharged through line 14 is passed to the vacuum pump receiver or a separator 15 which is generally operated at a slightly reduced pressure, with vapor being withdrawn through overhead vent 16, and liquid being withdrawn from the lower end through line 17. Usually the overhead vent 16 will consist mainly of ethylene and sulfur dioxide (as well as any nitrogen and oxygen than may have leaked into the system) since such light ends as ethyl acrylate, ethyl acetate, diethyl ether and ethanol present in light ends stream 10 are readily dissolved and absorbed into the seal fluid.

The liquid stream removed as bottoms from separator 15 is passed to distillation tower 13 wherein removal of components dissolved in the normally liquid hydrocarbon is accomplished. Due to the difference in volatilities of the normally liquid hydrocarbon and of the dissolved light ends, the required separation may be accomplished in a distillation tower having only a few trays. For example, a tower having only about three trays will generally provide satisfactory performance, although more trays may be utilized if desired. Removed overhead of distillation tower 13 through line 21 is a gaseous stream containing substantially all of the sulfur dioxide absorbed in the liquid, as well as such organic light ends as ethylene, ethyl acrylate, ethyl acetate, diethyl ether and ethanol, and as well as any nitrogen and oxygen present. A normally liquid hydrocarbon stream of improved purity, and being substantially free of any sulfur dioxide, is then removed as bottoms through line 12 and recycled to vacuum pump 11.

The distillation performed in distillation tower 13 does not have to remove all of the light ends dissolved in the normally liquid hydrocarbon, although it is preferred that substantially all of the sulfur dioxide be removed in the distillation. For example, the recycle stream 12 can contain a relatively large amount of organic light ends, for example from about 15% to 45% by weight, and still perform satisfactorily as a seal fluid. Generally the distillation should be under such conditions that the recycle stream (line 12) is substantially free of sulfur dioxide and does not contain in excess of about 40% by weight of ethyl acrylate, and preferably should be such that the recycle stream contains from about 20% to 30% by weight of ethyl acrylate. Small amounts of other organic light ends will usually also be present in the recycle stream in addition to the ethyl acrylate, and these are usually present in amounts which are about one-fifth or so of the amount of ethyl acrylate present. Although such would generally be uneconomical, the distillation could be performed to provide a recycle stream 12 which was substantially free of ethyl acrylate and other light ends; however, as pointed out above, such would be uneconomical and is not necessary to provide good results.

The distillation to remove or purge light ends from the normally liquid hydrocarbon is necessary because an undue or excess build-up of dissolved light ends would cause a rise in the vapor pressure of the recycled liquid; and if the vapor pressure of the recycled liquid were to become higher than the reduced pressure being provided by the vacuum pump, then the liquid would start to vaporize in the vacuum pump instead of providing the required liquid seal.

The distillation to remove dissolved light ends can be accomplished over a wide variety of conditions as will be appreciated by those skilled in the art. It is preferred to conduct the distillation at elevated temperatures within the range of about 170° to 250° F. and at reduced pressures of about 0.50 to 0.95 atmospheres absolute. The required heat may be supplied by reboiler 18. Reboiler 18 is in a forced circulation system, this being necessary because of the wide difference in boiling points between the light ends and the normally liquid hydrocarbon seal fluid. Distillation tower 13 will generally require only a few trays as pointed out above, but more can be used if desired.

The distillation is more readily accomplished if the feed through line 17 is preheated, and this may be accomplished by use of a heat exchanger 19 wherein heat from the recycle stream 12 is used for preheating the feed. This also accomplishes the dual purpose of cooling the recycle stream 12, which is desirable, and in most instances it will be desirable to further cool recycle stream 12 by means of a cooler 20. It is necessary that the recycle stream be cooled sufficiently to prevent vaporization in the vacuum pump. The temperature of recycle stream 12 fed to vacuum pump 11 should be generally within the range of about 50° to 90° F. The weight ratio of recycle stream 12 to the gaseous light ends stream 10, both of which are fed to vacuum pump 11, should generally be within the range of about 20:1 to 100:1, preferably 25:1 to 75:1.

EXAMPLE

In apparatus of the type illustrated in FIG. 1, there was passed to vacuum pump 11 through line 10 about 1,000 pounds per hour of gaseous light ends from the ethyl acrylate process. The gases flowing through line 10 were at a temperature of about 55° F. and a pressure of about 15 psia, and contained, by weight, about 13% ethyl acrylate, 36% ethylene, 0.5% ethyl acetate, 2% diethyl ether, 1% ethanol, 22% sulphur dioxide, 19.6% nitrogen and 5.9% oxygen. The nitrogen and oxygen were derived from air leaks in the vacuum system. The vacuum pump 11 was a rotary compressor type of pump.

Also passed through vacuum pump 11 was a liquid recycle stream 12 comprising about 50,000 pounds per hour of recycled liquid seal fluid. The composition of the recycled liquid seal fluid was about 70% per weight of a normally liquid hydrocarbon known by the tradename of "KerMac 600 W" and 25% by weight of ethyl acrylate, the remaining 5% being other miscellaneous organic light ends. "KerMac 600 W" is a tradename for a normally liquid hydrocarbon produced by Kerr-McGee Oil Company which boils within the range of about 500° to 600° F., contains about 17% by weight of aromatic and about 83% by weight of aliphatics (such 83% being the total of 35% paraffinic hydrocarbons and 48% napthenic hydrocarbon), and has a viscosity of 6.7 centistokes at 70° F. and 4.3 centistokes at 100° F.

The resulting gas liquid mixture was discharged from vacuum pump 11 and passed to separator 15 in order to separate the liquids from the gases. The separator 15 was operated at a pressure of about 10 psia. Removed overhead through vent line 16 was about 200 pounds per hour of vent gases containing, by weight, about 20% ethylene, 10% sulphur dioxide and 67% nitrogen and 3% oxygen. The approximate 50,800 pounds per hour of liquid removed through line 17 was at a temperature of about 85° F., but after passing through heat exchanger 19 the temperature of the liquid was elevated to about 185° F. before being fed to distillation tower 13.

The distillation tower 13 was a three tray stripper tower and the liquid from line 17 was fed onto the top tray. The tower was operated at an overhead pressure of about 12 psia and an overhead temperature of about 190° F. Removed through overhead vent 21 was about 800 pounds per hour of a gaseous light end stream containing, by weight, about 25% sulphur dioxide, 17% ethyl acrylate, 42% ethylene, 0.5% ethyl acetate, 2% diethyl ether, 0.5% ethanol, 7% nitrogen and 6% oxygen. The temperature of the bottom stream removed from distillation tower 13 through line 12 was about 230° F.; however, the temperature of this streaam was reduced to about 70° F. in heat exchanger 19 and cooler 20 prior to being recycled to vacuum pump 11. As pointed out above this recycle stream 12 consisted mainly of about 70% by weight of the normally liquid hydrocarbon, 25% by weight of ethyl acrylate, and 5% by weight other light ends, and there was no detectable amount of sulphur dioxide present in this recycle stream. The recycle stream 12 also contained about 0.2% by weight of phenothiazine which acted as a polymerization inhibitor. The phenothiazine had been added to the liquid seal fluid prior to its being added to the system.

The foregoing Example should not be taken as limiting the invention and is only intended to be illustrative of a process conducted in accordance with the invention. In the Example there is disclosed the use of phenothiazine as a polymerization inhibitor, and it is necessary that such an inhibitor be present in the system to prevent polymerization of the ethyl acrylate and other unsaturates present. If the polymerization inhibitor is not present severe polymerization problems will occur and cause plugging and other damage to equipment. Any of the standard polymerization inhibitors, such as hydroquinone and phenothiazine, may be used. Those skilled in the art will be aware of various others that are and would be operative. The amount of the polymerization inhibitor required is generally very small and need only be a polymerization inhibiting amount, and the exact amount will vary according to the particular compound being utilized. Solubility limits of the polymerization inhibitor should not be exceeded since precipitation of the inhibitor may cause problems in the process.

The embodiments of the invention in which an exclusive claim or privilege is claimed are:

1. In a process for the production of ethyl acrylate by the reaction of ethylene with acrylic acid in the presence of a sulfuric acid catalyst wherein the reaction products are distilled in a vacuum distillation system at a reduced pressure less than atmospheric to obtain a liquid ethyl acrylate product and also resulting in a first gaseous light ends stream from said vacuum distillation system containing sulfur dioxide and also containing ethylene, ethyl acrylate and other organic light ends by-products, which said first gaseous light ends stream passes through a vacuum pump providing the reduced pressure for said vacuum distillation system, which said vacuum pump utilizes a liquid seal fluid to provide a liquid seal therein and in which said vacuum pump said first gaseous light ends stream mixes with and is partially absorbed in said liquid seal fluid to result in a gas-liquid mixture which is discharged from said vacuum pump, and which said gas-liquid mixture so discharged is fractionated to recover a liquid recycle stream comprising liquid seal fluid and which said liquid recycle stream is recycled to said vacuum pump, the improvements which comprise (a) utilizing as said liquid seal fluid a normally liquid hydrocarbon which has a minimum boiling point of 425° F. and 90% by weight of which boils within the range of about 425° F. to 800° F., and (b) fractionating said gas-liquid mixture so discharged as to recover a said liquid recycle stream comprising said liquid seal fluid which is substantially free of sulfur dioxide and does not contain in excess of about 40% by weight of ethyl acrylate.

2. The process of claim 1 wherein said normally liquid hydrocarbon contains at least 50% by weight of non-aromatic hydrocarbons.

3. The process of claim 1 wherein said normally liquid hydrocarbon contains less than 5% by weight of ethylenically and acetylenically unsaturated compounds.

4. The process of claim 1 wherein the weight ratio of said liquid recycle stream to said first gaseous light ends stream is within the range of about 20:1 to 100:1.

5. The process of claim 1 wherein the said liquid recycle stream is cooled to a temperature within the range of about 50° F. to 90° F. prior to being introduced to said vacuum pump.

6. The process of claim 1 wherein said gas-liquid mixture discharged from said vacuum pump is fractionated to recover said liquid recycle stream comprising said liquid seal fluid by passing said gas-liquid mixture to a gas-liquid separator, removing a gaseous stream overhead from said separator and removing as bottoms from said separator a liquid stream comprising said liquid seal fluid having sulfur dioxide, ethyl acrylate and other organic light ends absorbed therein, passing said liquid stream removed as bottoms from said separator to a stripper distillation tower which is operated under such conditions as to remove overhead from said stripper distillation tower a gaseous stream containing ethyl acrylate and other organic light ends and also containing substantially all of the sulfur dioxide passed to said stripper distillation tower, and so as to remove as bottoms from said stripper distillation tower a said liquid recycle stream comprising said liquid seal fluid having about 20% to 30% by weight of ethyl acrylate absorbed therein and being substantially free of sulfur dioxide.

7. The process of claim 6 wherein said normally liquid hydrocarbon contains at least 50% by weight of non-aromatic hydrocarbons.

8. The process of claim 6 wherein said normally liquid hydrocarbon contains less than 5% by weight of ethylenically and acetylenically unsaturated compounds.

9. The process of claim 6 wherein the weight ratio of said liquid recycle stream to said first gaseous light ends stream is within the range of about 25:1 to 75:1.

10. The process of claim 9 wherein the said liquid recycle stream is cooled to a temperature within the range of about 50° F. to 90° F. prior to being introduced to said vacuum pump.

11. The process of claim 1 wherein there is present in said liquid recycle stream a polymerization inhibiting amount of a polymerization inhibitor.

12. The process of claim 6 wherein there is present in said liquid recycle stream a polymerization inhibiting amount of a polymerization inhibitor.

13. The process of claim 9 wherein there is present in said liquid recycle stream a polymerization inhibiting amount of a polymerization inhibitor.

* * * * *